US012257261B2

(12) United States Patent
Picker et al.

(10) Patent No.: US 12,257,261 B2
(45) Date of Patent: Mar. 25, 2025

(54) PREPARATION OF PRELIPOSOMAL ANNAMYCIN LYOPHILIZATE

(71) Applicants: Board of Regents, The University of Texas System, Austin, TX (US); Moleculin Biotech, Inc., Houston, TX (US)

(72) Inventors: Donald Picker, Albany, NY (US); Waldemar Priebe, Houston, TX (US)

(73) Assignees: Board of Regents, The University of Texas System, Austin, TX (US); Moleculin Biotech, Inc., Houston, TX (US)

(*) Notice: Subject to any disclaimer, the term of this patent is extended or adjusted under 35 U.S.C. 154(b) by 495 days.

(21) Appl. No.: 17/554,550

(22) Filed: Dec. 17, 2021

(65) Prior Publication Data

US 2022/0105115 A1    Apr. 7, 2022

Related U.S. Application Data

(63) Continuation of application No. PCT/US2020/039620, filed on Jun. 25, 2020.

(60) Provisional application No. 62/868,184, filed on Jun. 28, 2019.

(51) Int. Cl.

| A61K 31/704 | (2006.01) |
|---|---|
| A61K 9/08 | (2006.01) |
| A61K 9/16 | (2006.01) |
| A61K 9/19 | (2006.01) |
| A61K 47/20 | (2006.01) |
| A61K 47/24 | (2006.01) |
| A61K 47/26 | (2006.01) |

(52) U.S. Cl.
CPC .............. *A61K 31/704* (2013.01); *A61K 9/08* (2013.01); *A61K 9/1694* (2013.01); *A61K 9/19* (2013.01); *A61K 47/20* (2013.01); *A61K 47/24* (2013.01); *A61K 47/26* (2013.01)

(58) Field of Classification Search
CPC .................................................. A61K 31/704
See application file for complete search history.

(56) References Cited

U.S. PATENT DOCUMENTS

| 4,863,739 | A | 9/1989 | Perez-Soler | |
|---|---|---|---|---|
| 5,902,604 | A * | 5/1999 | Zou | A61K 9/1277 |
| | | | | 264/4.1 |
| 7,238,366 | B1 * | 7/2007 | Zou | A61K 9/1277 |
| | | | | 264/4.1 |
| 11,980,634 | B2 | 5/2024 | Picker | |
| 2004/0057989 | A1 | 3/2004 | Andreeff | |
| 2005/0238707 | A1 | 10/2005 | Andreeff | |
| 2013/0195963 | A1 | 8/2013 | Serda | |
| 2014/0308339 | A1 | 10/2014 | Ryan | |
| 2016/0175438 | A1 | 6/2016 | Alavattam | |
| 2017/0209574 | A1 | 7/2017 | Cao | |
| 2017/0281624 | A1 | 10/2017 | Peters | |
| 2022/0105116 | A1 | 4/2022 | Picker | |

FOREIGN PATENT DOCUMENTS

| WO | 1988009168 | 12/1988 |
|---|---|---|
| WO | 1996039121 | 12/1996 |
| WO | 2001032145 | 5/2001 |
| WO | 2018048752 | 3/2018 |
| WO | 2020264160 | 12/2020 |
| WO | 2020264161 | 12/2020 |
| WO | 2021102404 | 5/2021 |

OTHER PUBLICATIONS

Bulbake, U. et al., "Liposomal Formulations in Clinical Use: An Updated Review", Pharmaceutics, 9(2): 12, (2017).
Hanawa, T. et al., Medicine, vol. 74(1):57-62, (2014).
International Application No. PCT/US2020/039620; International Preliminary Report on Patentability, date of issuance Jan. 6, 2022; 7 pages.
International Application No. PCT/US2020/039620; International Search Report and Written Opinion of the International Searching Authority, date of mailing Oct. 1, 2020; 10 pages.
International Application No. PCT/US2020/039621; International Preliminary Report on Patentability, date of issuance Jan. 6, 2022; 6 pages.
International Application No. PCT/US2020/039621; International Search Report and Written Opinion of the International Searching Authority, date of mailing Oct. 1, 2020; 8 pages.
International Application No. PCT/US2020/061775; International Preliminary Report on Patentability, date of issuance Jun. 9, 2022; 6 pages.
International Application No. PCT/US2020/061775; International Search Report and Written Opinion of the International Searching Authority, date of mailing Feb. 11, 2021; 8 pages.
Lauraeus, S. et al., "Aggregation of dimyristoylphosphatidylglycerol liposomes by human plasma low density lipoprotein", 1373(1):147-62, (1998).
Moleculin Biotech, Inc., "Moleculin Announces Significant Discovery in Lung Cancer Models", PR Newswire, retrieved at https://www.prnewswire.com/news-releases/moleculin-announces-significant-discovery-in-lung-cancer-models-300833462.html, 3 pages, (dated Apr. 2019).
Moleculin, "Moleculin Increases Annamycin Production Due to Positive Clinical Trial Activity and Expanded Potential Indications", created Oct. 22, 2019.
Pérez-Herrero, E. et al., "Advanced targeted therapies in cancer: Drug nanocarriers, the future of chemotherapy", Eur J Pharm Biopharm., 93:52-79, (2015).

(Continued)

*Primary Examiner* — Carlos A Azpuru
(74) *Attorney, Agent, or Firm* — Global Patent Group Inc.; Cynthia Hathaway; Erik M. Larsen

(57) ABSTRACT

Provided is a method of making a preliposomal Annamycin lyophilizate, the composition made by the method, and the use of the composition made thereby in the treatment of cancer.

17 Claims, No Drawings

(56) References Cited

OTHER PUBLICATIONS

Perez-Soler, R. et al., "Annamycin circumvents resistance mediated by the multidrug resistance-associated protein (MRP) in breast MCF-7 and small-cell lung UMCC-1 cancer cell lines selected for resistance to etoposide", Int J Cancer, 71(1):35-41, (1997).

Perez-Soler, R., "Treatment of Metastatic Breast Carcinoma Refractory to Doxorubicin With Liposomal-Annamycin", US Army Med Res Mat Command Annual Report, pp. 5-16, 24-34, (1997).

Zou, Y. et al., "Antitumor Activity of Free and Liposome-entrapped Annamycin, a Lipophilic Anthracycline Antibiotic with Non-Cross-Resistance Properties", Cancer Res., 54(6):1479-84, (1994).

Zou, Y. et al., "Antitumor Activity of Free and Liposome-entrapped Annamycin, a Lipophilic Anthracycline Antibiotic with Non-Cross-Resistance Properties", Cancer Res., 54(6):1479-84, Abstract only, (1994).

Zou, Y. et al., "Lyophilized Preliposomal Formulation of the Non-Cross-Resistant Anthracycline Annamycin: Effect of Surfactant on Liposome Formation, Stability and Size", Cancer Chemother Pharmacol., 39(1-2):103-8, (1996).

Zou, Y. et al., "Organ distribution and tumor uptake of annamycin, a new anthracycline derivative with high affinity for lipid membranes, entrapped in multilamellar vesicles", Cancer Chemother Pharmacol., 32(3):190-6, (1993).

Zou, Y. et al., "Organ distribution and tumor uptake of annamycin, a new anthracycline derivative with high affinity for lipid membranes, entrapped in multilamellar vesicles", Cancer Chemother Pharmacol., 32(3):190-6, Abstract only, (1993).

Zou, Y. et al., "Preclinical toxicity of liposome-incorporated annamycin: selective bone marrow toxicity with lack of cardiotoxicity", Clin Cancer Res., 1(11):1369-74, (1995).

Cullis, P. et al., "Generating and loading of liposomal systems for drug-delivery applications", Adv Drug Deliv Rev., 3:267-82, (1989).

U.S. Appl. No. 17/554,553; Applicant-Initiated Interview Summary, date of interview Nov. 12, 2024; 3 pages.

U.S. Appl. No. 17/554,553; Non-Final Office Action, dated Aug. 29, 2024; 14 pages.

Wetzler, M. et al., "Phase I/II trial of nanomolecular liposomal annamycin in adult patients with relapsed/refractory acute lymphoblastic leukemia", Clin Lymphoma Myeloma Leuk., 13(4):430-4, (2013).

* cited by examiner

PREPARATION OF PRELIPOSOMAL ANNAMYCIN LYOPHILIZATE

This application is a bypass continuation of International Application No. PCT/US2020/039620, filed Jun. 25, 2020, which claims the benefit of priority of U.S. Provisional Application No. 62/868,184, filed Jun. 28, 2019, the disclosures of which are hereby incorporated by reference as if written herein in their entireties.

Annamycin is a cancer chemotherapeutic agent of the anthracycline structural family. Because of its physical and pharmacological properties, compositions of Annamycin for dosage forms have been described in which the drug is formulated as a liposome (See U.S. Pat. No. 7,238,366). Clinical trials have been described for liposomal Annamycin in adult patients with relapsed refractory Acute lymphoblastic leukemia (M. Wetzler, et al., Clinical Lymphoma, Myeloma and Leukemia, 13 (4), 430-434 August 2013) and in the treatment of doxorubicin-resistant breast cancer (D. J. Booser et al., Cancer Chemother. Pharmacol. 50; 6-8, 2002).

In drug delivery systems, it is desirable to be able to produce a drug formulation that is of consistently purity and quality in order to ensure that the correct dosage is administered, thus providing the most efficacious treatment, while avoiding unwanted side effects caused by impurities. Furthermore, poorly maintained or improperly formulated drug material can decompose prior to administration, rendering them ineffective, resulting in waste of costly active pharmaceutical ingredients. Regulatory standards also necessitate that a consistent level of purity of drug and amount of drug be provided by following the procedures specified on the label.

Annamycin presents particularly difficult formulation challenges because of its inherent physical properties, and because of inherent instability of both the parent drug and of liposomal formulation under certain conditions. Liposomal formulations of Annamycin commonly degrade and form Annamycin crystals, and/or develop large liposomes or phase separation making the formulation unsuitable for administration. It would therefore be advantageous to find a consistent method for preparing a dosage form of preliposomal Annamycin that assures purity and avoids decomposition of the Annamycin.

SUMMARY

Provided is a method of making lyophilized Annamycin comprising the steps of:
  making a solution comprising one or more lipids, one or more non-ionic surfactants, and one or more solvents and having a pH of 4.8-5.9;
  adding to the lipid solution an Annamycin solution comprising about 8-12 wt. % Annamycin in DMSO to provide a lipid containing solution of Annamycin;
  sterile filtering the lipid containing solution of Annamycin; and
  lyophilizing the lipid containing solution of Annamycin to provide a preliposomal Annamycin lyophilizate.

Provided is a method of producing a lyophilized Annamycin comprising the steps of:
  making a first solution comprising water and t-butanol wherein the ratio of water to t-butanol is from about 8:2 to about 9:1;
  adding one or more lipids and one or more non-ionic surfactants to the first solution to form a second solution;
  adjusting the pH of the second solution such that the pH is 4.8-5.9;
  adding a third solution comprising about 8-12 wt. % Annamycin in DMSO to the second solution to provide a lipid containing solution of Annamycin;
  sterile filtering the lipid containing solution of Annamycin; and
  lyophilizing the lipid containing solution of Annamycin to provide a preliposomal Annamycin lyophilizate.

Also provided is a method of producing Annamycin preliposomal lyophilizate, comprising the steps of:
  adding of DMPC, DMPG and polysorbate 20 to a mixture of pre-warmed water and t-butanol to prepare a first solution, wherein the prewarmed temperature is from about 35° C. to about 42° C., and wherein the ratio of water to t-butanol is from about 8:2 to about 9:1;
  adjusting the pH of the first solution with pharmaceutically acceptable acid, such that the pH of the solution remains constant for at least 15 minutes;
  adding a second solution comprising approximately 8-12 wt % of Annamycin in DMSO to the first solution, to provide a lipid containing solution of Annamycin;
  sterile filtering the lipid containing solution of Annamycin; and
  lyophilization of the lipid containing solution of Annamycin in individual aliquots to provide a preliposomal lyophilizate.

Also provided is a preliposomal Annamycin lyophilizate prepared by any of the methods described herein.

Also provided is a method of treating cancer comprising administering to a patient in need thereof, an effective dose of liposomal Annamycin prepared using the preliposomal Annamycin lyophilizate prepared by any of the methods described herein.

Also provided is a use of preliposomal Annamycin lyophilizate prepared according to any of the methods described herein, in the manufacture of a medicament for the treatment of cancer.

Also provided is a preliposomal Annamycin lyophilizate prepared according to any of the methods described herein, for use in the treatment of cancer.

DETAILED DESCRIPTION

Provided is a method of making a preliposomal Annamycin lyophilizate with improved stability and high purity. This preliposomal Annamycin lyophilizate composition can be reconstituted into an aqueous liposome composition through hydration, as described in U.S. Pat. No. 7,238,366 which is incorporated by reference in its entirety for all purposes, for example, and then used to treat cancer.

Unless defined otherwise, all technical and scientific terms used herein have the same meaning as is commonly understood by one of skill in the art to which the invention(s) belong.

As used herein, the following terms have the meaning as defined below.

The term "Annamycin" shall mean the compound, (7S, 9S)-7-(((2R,3R,4R,5R,6S)-4,5-dihydroxy-3-iodo-6-methyl-tetrahydro-2H-pyran-2-yl)oxy)-6,9,11-trihydroxy-9-(2-hydroxyacetyl)-7,8,9,10-tetrahydrotetracene-5,12-dione, having the following structure:

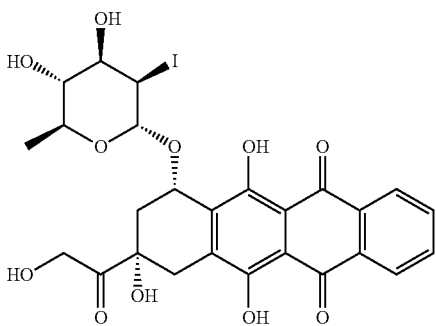 [SMILES: C[C@@H]1O[C@@H](O[C@H]2C[C@](O)(C(=O)CO)Cc3c(O)c4c(c(O)c32)C(=O)c2ccccc2C4=O)[C@H](I)[C@H](O)[C@H]1O]

The term "high purity Annamycin preliposomal lyophilizate" shall mean purity of material which is no less than 95% Annamycin as analyzed by HPLC using a verified standard sample. In some embodiments, the Annamycin is at least 96% pure, or at least 97% pure, or at least 98% pure, or at least 99% pure.

The term "liposomes," "liposomal," and the like shall mean generally spherical structures comprising lipids, fatty acids, lipid bilayer type structures, unilamellar vesicles and amorphous lipid vesicles. Classically, liposomes are completely closed lipid bilayer membranes containing an entrapped aqueous volume. Liposomes include non-classical forms where the Annamycin may be inside the bilayer, part of the bilayer and absorbed onto the bilayer. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The term "preliposome-lyophilizate" and "preliposomal lyophilizate" shall mean a non-aqueous material that will form liposomes upon addition of aqueous solution. In some embodiments the non-aqueous material is dry (as in non-liquid, non-gel) material. Lyophilizate is used expansively to include the dry residue of sublimation of frozen liquids from non-volatile materials, the residue of roto evaporation and similar procedures, and dry compositions that, upon addition of an aqueous phase (with or without agitation) with result in liposomes. It is particularly to be understood that "preliposome-lyophilizate" is not in liposomal form after lyophilization.

The term "lipids" refers to any of a class of pharmaceutically acceptable organic compounds that are fatty acids or their derivatives. In some embodiments, the lipids are phospholipids, such as phosphatidylcholines including DMPC and DPMG, but may also include other lipids, such as egg phosphatidylethanolamine.

The term "non-ionic surfactants" refers to pharmaceutically acceptable surfactants that have covalently bonded oxygen-containing hydrophilic groups, which are bonded to hydrophobic parent structures. Suitable non-ionic surfactants include ethoxylates, fatty alcohol ethoxylates, alklphenol ethoxylates, fatty acid ethoxylates, ethoxylated fatty esters and oils, ethoxylated amines, fatty acid amides, terminally blocked ethoxylates, poloxamers, fatty acid esters of polyhydroxy compounds, fatty acid esters of glycerol, and fatty acid esters of sorbitol. In some embodiments, the non-ionic surfactants are polysorbate-type surfactants formed from the ethoxylation of sorbitan followed by the addition of a carboxylic acid. In some embodiments, the non-ionic surfactant comprises polyoxyethylene sorbitan monolaurate (Polysorbate 20), and polyethoxylated sorbitan monooleic acid (Polysorbate 80).

"Polysorbate 20" refers to a commercially available non-ionic surfactant (ICI Americas Inc.) consisting of a mixture of different length chains of polyoxyethylene linked to a common sorbitan sugar. These polyoxyethylene sugars are also linked to a fatty acid. A tradename for this material is Tween™ 20; the composition is polyoxyethylene sorbitan monolaurate (MW approximately 1300). As Polysorbate 20 is shown below, $w+x+y+z=20$.

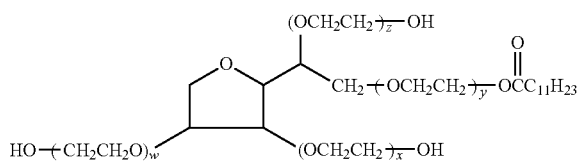

The term "pharmaceutically acceptable acid" refers to any organic and inorganic acid that is known in the art to be well tolerated and suitable for administration to human patients. Such salts include 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), undecylenic acid. Pharmaceutically acceptable acids include hydrochloric acid and sulfuric acid.

In the foregoing sections, a number of abbreviations and acronyms were used, and the full description of these are provided as follows:
DMPC dimyristoyl phosphatidylcholine
DMPG 1,2-dimyristoyl-sn-glycero-3-[phospho-(1'-rac-glycerol) (sodium salt)
DMSO dimethyl sulfoxide
IV intravenous
DEHP bis(2-ethylhexyl) phthalate
PVC polyvinyl chloride
WPI Water for Injection, USP Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps. It is intended herein that by recitation of such specified ranges, the ranges recited also include all those specific integer amounts between the cited ranges. For example, the range of about 35-42° C., it is intended to also encompass 35, 36, 37, 38, 39, 40, 41 and 42° C.

The entire disclosure of each United States patent and international patent application mentioned in this patent specification is fully incorporated by reference herein for all purposes.

Provided is a method of making a preliposomal Annamycin lyophilizate that has superior purity and stability. In particular, provided is a method of making a lyophilized Annamycin comprising the steps of:

making a first solution comprising water and t-butanol wherein the ratio of water to t-butanol is from about 8:2 to about 9:1;

adding one or more lipids and one or more non-ionic surfactants to the first solution to form a second solution;

adjusting the pH of the second solution such that the pH is 4.8-5.9;

adding a third solution comprising about 8-12 wt. % Annamycin in DMSO to the second solution to provide a lipid containing solution of Annamycin;

sterile filtering the lipid containing solution of Annamycin; and lyophilizing the lipid containing solution of Annamycin to provide a preliposomal Annamycin lyophilizate.

In some embodiments, the second solution comprises DMPC, DMPG, and a polyoxyethylene sorbitan surfactant. In some embodiments, the second solution comprises DMPC, DMPG, and polyoxyethylene sorbitan monolaurate.

In some embodiments, each of the lipids and each of the non-ionic surfactants are added individually.

In some embodiments, DMPC, DMPG, and polyoxythylene sorbitan monnolaurate are added sequentially to the first solution.

In some embodiments, the method comprising adjusting the pH of the second solution to 5.3±0.2 with a pharmaceutically acceptable acid selected from the group consisting of HCl and $H_2SO_4$.

In some embodiments, the method comprising adding a third solution comprising about 10 wt. % Annamycin in DMSO to the second solution to provide a lipid containing solution of Annamycin.

In some embodiments, the preliposomal Annamycin lyophilizate comprises: 1.8-2.2 wt % Annamycin; 3.0-3.4 wt. % Polysorbate 20; and 94.4-95.2 wt. % of lipids selected from DMPC and DMPG. In some embodiments, the DMPC is 65.3-67.3 wt. % and the DMPG is 27.1-29.9 wt. %.

In some embodiments, the Annamycin in the lyophilizate produced is at least 98% pure. In some embodiments, the Annamycin in the lyophilizate produced is a least 99% pure.

In some embodiments, the method of making a lyophilized Annamycin comprising the steps of:

making a first solution comprising water and t-butanol wherein the ratio of water to t-butanol is from about 8:2 to about 9:1;

adding one or more lipids and one or more non-ionic surfactants to the first solution to form a second solution that comprises DMPC, DMPG, and Polysorbate 20;

adjusting the pH of the second solution such that the pH is 5.3±0.2;

allowing the solution to equilibrate for at least 15 minutes;

measuring the pH and adjusting the pH with acid if the pH is above 5.3 allowing the solution to equilibrate for at least 15 minutes;

repeating the steps of measuring the pH, adjusting the pH, and allowing the solution to equilibrate until the pH of the solution remains at pH 5.3±0.2;

adding a third solution comprising about 8-12 wt. % Annamycin in DMSO to the second solution to provide a lipid containing solution of Annamycin;

sterile filtering the lipid containing solution of Annamycin; and lyophilizing the lipid containing solution of Annamycin to provide a lipid containing Annamycin lyophilizate.

In some embodiments, the acid used to adjust the pH is selected from the group consisting of HCl, and $H_2SO_4$. In some embodiments, the acid is HCl, such as 1M HCl.

In some embodiments, the method further comprises measuring the pH after the addition of the Annamycin containing solution, and adjusting the pH to 5.3±0.2 if necessary.

In some embodiments, the lipid containing solution is allowed to equilibrate for at least 30 minutes after each addition of acid. In some embodiments, the lipid containing solution is allowed to equilibrate for about 45 minutes after each addition of acid.

In some embodiments, each solution is maintained at a temperature of from about 38° C. to about 42° C. until lyophilization is started.

In some embodiments, a preliposomal Annamycin lyophilizate is produced comprising the steps of:

adding DMPC, DMPG and polysorbate 20 to a mixture of pre-warmed water and t-butanol to prepare a first solution, wherein the prewarmed temperature is from about 35° C. to about 42° C., and wherein the ratio of water to t-butanol is from about 8:2 to about 9:1;

adjusting the pH of the first solution with one or more pharmaceutically acceptable acids, such that the pH of the solution remains constant for about 15-90 minutes;

adding a second solution comprising approximately 8-12 wt. % of Annamycin in DMSO to the first solution, to provide a lipid containing solution;

sterile filtering the lipid containing solution; and lyophilizing the lipid containing solution of Annamycin in individual aliquots to provide a preliposomal lyophilizate.

In some embodiments, the method comprising adjusting the pH of the first solution to 5.3±0.2 with a pharmaceutically acceptable acid selected from the group consisting of HCl and $H_2SO_4$.

In some embodiments, the method comprising adding a second solution comprising about 10 wt. % Annamycin in DMSO to the second solution to provide a lipid containing solution of Annamycin.

In some embodiments, the preliposomal Annamycin lyophilizate comprises: 1.8-2.2 wt % Annamycin; 3.0-3.4 wt. % Polysorbate 20; and 94.4-95.2 wt. % of lipids selected from DMPC and DMPG. In some embodiments, the DMPC is 65.3-67.3 wt. % and the DMPG is 27.1-29.9 wt. %.

In some embodiments, the Annamycin in the lyophilizate produced is at least 98% pure. In some embodiments, the Annamycin in the lyophilizate produced is a least 99% pure.

Also provided is a a composition of preliposomal Annamycin prepared by any of the methods described herein, and comprises 1.8-2.2 wt % Annamycin; 3.0-3.4 wt. % Polysorbate 20; and 94.4-95.2 wt. % of lipids selected from DMPC and DMPG. In some embodiments, the DMPC is 65.3-67.3 wt. % and the DMPG is 27.1-29.9 wt. %.

In some embodiments, the composition of preliposomal Annamycin lyophilizate is at least 98% pure.

Also provided is a process to prepare a lipid containing solution of Annamycin by addition of a DMSO solution of Annamycin to a pH adjusted solution comprising DMPG, DMPC and Polysorbate 20 in water/t-butanol, wherein the pH is maintained at pH 4.8-5.9 for 15-75 minutes. In another embodiment, the pH is maintained at 5.3+/−0.2. In another embodiment the pH is maintained for about 45 minutes.

Also provided is a process to prepare individual practicable quantities of high purity Annamycin preliposomal lyophilizate, such process including lyophilizing premeasured individual aliquots of the lipid containing solution for about 48 h.

A specific embodiment includes the preparation of high purity Annamycin preliposomal lyophilizate in which the individual practicable quantities are prepared in 50 mL vials containing 45 mg of Annamycin.

Also provided is a method of treating cancer comprising administering to a patient in need thereof, an effective dose of liposomal Annamycin prepared using the preliposomal Annamycin lyophilizate prepared by any of the methods described herein.

In some embodiments, there is provided a use of preliposomal Annamycin lyophilizate prepared according to any of the methods described herein, in the manufacture of a medicament for the treatment of cancer.

In some embodiments, there is provided a preliposomal Annamycin lyophilizate prepared according to any of the methods described herein, for use in the treatment of cancer.

General Experimental Methods

Dimyristoyl phosphatidylcholine (DMPC) and 1,2-dimyristoyl-sn-glycero-3-[phosphor-rac-(1 glycerol)] sodium salt (DMPG) were each obtained as a dry powder from Nippon Fine Chemicals, Inc., Osaka, Japan.

Annamycin (>95% pure) (MW=640.39) was synthesized as previously described with slight modifications (Horton, D., Priebe, W. 4-demethoxy-3'-desamino-2'-halo-anthracyclines and pharmaceutical compositions containing same. U.S. Pat. No. 4,537,882, 1985.)

Polysorbate 20, DMSO, chloroform and t-butyl alcohol were obtained from Aldrich Chemical Company, Inc., Milwaukee, Wis. Normal saline was obtained from Abbott Laboratories, North Chicago, Ill.

Dosages and Routes of Administration.

The preliposomal lyophilizate powder of Annamycin is used to prepare, generally on the day of administration, an effective dose of liposomal Annamycin, for example, suspended in saline in a non-PVC IV bag. The stability of the liposomal solution requires storage of the drug as a preliposomal lyophilizate maintained at low temperature (frozen in −80° C.-0° C. storage) until just prior to administration, and once formed, should be used within 24 h or discarded. Liposomal Annamycin is used in methods of treating cancer and in methods of inhibiting the growth of tumors in mammals, particularly in humans. Cancer that may be treated include leukemias and lymphomas. In particular, Annamycin may be used in the treatment of leukemias including acute myeloid leukemia (AML), chronic myeloid leukemia (CML), acute lymphocytic leukemia (ALL), and chronic lymphocytic leukemia (CLL). Liposomal Annamycin may be used in the treatment of lymphomas including Hodgkin and non-Hodgkin lymphoma.

The methods involve administering to a mammal an effective amount of drug compositions. The administering step can suitably be parenteral and by intravenous, intraarterial, intramuscular, intralymphatic, intraperitoneal, subcutaneous, intrapleural, intrathecal injection, or by topical application dosage. In some embodiments, such administration is repeated regimen until tumor regression or disappearance is achieved, and may be used in conjunction with forms of tumor therapy such as surgery or chemotherapy with different agents. In some embodiments, the dose administered of a composition is between approximately 125 and 280 mg/m2 with respect the mammalian subject to which it is administered.

EXAMPLES

Embodiments will now be described by way of example only with respect to the following example.
General Procedures.

Example 1. Preparation of Annamycin Liposome Pre-Lyophilizate t-Butanol and WFI (Water for Injection) were warmed in a water bath at 40° C.±5° C. prior to use.

t-Butanol (9181.2 g±1%) was added to a 15 L beaker while stirring, and Water for Injection (WFi, 1465.8 g±1%) was added. During the addition, the beaker was maintained at −40° C. Approx. 2 L of the mixed solution was removed and place into a sterile beaker, to be used in succeeding steps as a "rinse" wash. Stirring of the bulk alcohol/water solution was continued.

DMPC (743.554 g±1%), contained in a beaker, was added to the bulk alcohol/water solution. After all the DMPC was added, a portion (approx. ¼) of the "rinse" liquid was used to wash out any remaining residue in the beaker, and the washings were added to the bulk mixture. The mixture was stirred until all material was dissolved.

DMPG sodium salt (318.654 g±1%), contained in a beaker, was added to the bulk alcohol/water solution. After all the DMPG was added, a portion (approx. ¼) of the "rinse" liquid was used to wash out any remaining residue in the beaker, and the washings were added to the bulk mixture. The entire mixture was stirred until all material was dissolved.

Polysorbate 20 (36.12 g±1%), contained in a 100 mL beaker, was carefully dispensed into the bulk solution. After all the Polysorbate 20 was added, a portion (approx. ¼) of the "rinse" liquid was used to wash out any remaining residue in the beaker, and the washings were added to the bulk mixture. The entire mixture was stirred until all material was dissolved, and maintained at 40+/−5° C.

The pH of the bulk solution was measured and adjusted to 5.3±0.2 with 1.0 M HCl. The pH was measured at 2-3 min intervals and again adjusted to 5.3±0.2 with 1.0 M HCl. This step was repeated until the pH of the mixture remained constant at pH about 5.3±0.2 for 2-3 min. The solution was then stirred for 45 minutes, the pH was again checked and adjusted to pH 5.3±0.2 with 1.0 M HCl if necessary. After stirring the mixture for an additional 45 min, the pH was measured. If necessary, the process of adjusting the pH is continued until the pH reading is at pH 5.3±0.2 after stirring for 2-3 min. When there was no change in pH from initial reading, the bulk solution was ready for further processing. Otherwise this step was repeated until the pH remains at pH 5.3±0.2 for about 45 minutes.

Annamycin (as the THF complex) was prepared in purified form (>98% by HPLC) following the procedure in U.S. Pat. No. 977,327 (Example VIII, Cols. 7-8).

To Annamycin (THF Complex, API, 23.16 g±1%) in a sterile beaker, was added DMSO (234.08 g±1%) and the materials were stirred until dissolved. The DMSO/API solution was added to the bulk solution with stirring and any remaining "rinse" liquid was added directly to the bulk solution and stirring was continued.

The solution was passed through sterile 0.2 micron filters two times. The filtered product solution was stored overnight at ambient temperature. The bulk volume of the product solution was approx. 13.83 L.

Filtered product solution, (25 mL by weight to be determined from density test performed as part of the in process testing), was filled into 50 mL clear glass lyophilization vials. Lyophilization was carried out for 48 h to remove all DMSO, t-butyl alcohol and water providing a preliposomal powder.

The purity of the Annamycin in the lyophilized powder was measured by HPLC using a verified reference standard sample.

While the invention has been described with reference to particular embodiments and examples, those skilled in the art recognize that various modifications may be made to the invention without departing from the spirit and scope thereof.

All references cited herein, including patents, patent applications, and publications, are incorporated herein by reference, in their entirety. Whether previously specifically incorporated or not.

The various features and embodiments of the present invention, referred to in individual section above apply, as appropriate, to other sections, mutatis mutandis. Consequently, features specified in one section may be combined with features specified in other sections, as appropriate.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for the purposes of limitation of the scope of the claims. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. A method of making lyophilized Annamycin comprising the steps of:
    making a solution comprising one or more lipids, one or more non-ionic surfactants, and one or more solvents and having a pH of 4.8-5.9 and wherein said one or more lipids includes DMPG with a pH adjusted to 4.8-5.9;
    adding to the lipid solution an Annamycin solution comprising about 8-12 wt. % Annamycin in DMSO to provide a lipid containing solution of Annamycin;
    sterile filtering the lipid containing solution of Annamycin; and
    lyophilizing the lipid containing solution of Annamycin to provide a preliposomal Annamycin lyophilizate wherein the Annamycin in the lyophilizate produced is at least 95% pure.

2. A method of making lyophilized Annamycin comprising the steps of:
    making a first solution comprising water and t-butanol wherein the ratio of water to t-butanol is from about 8:2 to about 9:1;
    adding one or more lipids and one or more non-ionic surfactants to the first solution to form a second solution and wherein one or more lipids includes DMPG;
    adjusting the pH of the second solution such that the pH is 4.8-5.9;
    adding a third solution comprising about 8-12 wt. % Annamycin in DMSO to the second solution to provide a lipid containing solution of Annamycin;
    sterile filtering the lipid containing solution of Annamycin; and
    lyophilizing the lipid containing solution of Annamycin to provide a preliposomal Annamycin lyophilizate wherein the Annamycin in the lyophilizate produced is at least 95% pure.

3. The method of claim 2 wherein the second solution comprises DMPC, DMPG, and a polyoxyethylene sorbitan surfactant.

4. The method of claim 3, wherein the second solution comprises DMPC, DMPG, and polyoxyethylene sorbitan monolaurate.

5. The method of claim 4, wherein the pH of the second solution is adjusted to $5.3\pm0.2$ with a pharmaceutically acceptable acid selected from the group consisting of HCl and $H_2SO_4$.

6. The method of claim 5, wherein the third solution comprises about 10 wt. % Annamycin in DMSO.

7. The method of claim 6, wherein each of the lipids and each of the surfactants are added individually.

8. The method of claim 7, wherein DMPC, DMPG, and polyoxythylene sorbitan monolaurate are added sequentially to the first solution.

9. The method of claim 8, wherein the preliposomal Annamycin lyophilizate comprises: 1.8-2.2 wt. % Annamycin; 3.0-3.4 wt. % Polysorbate 20; and 94.4-95.2 wt. % of lipids selected from DMPC and DMPG.

10. The method of claim 9, wherein the Annamycin in the lyophilizate produced is at least 98% pure.

11. The method of claim 10, wherein the Annamycin in the lyophilizate produced is at least 99% pure.

12. The method of claim 4, further comprising:
    after initially adjusting the pH of the second solution to pH $5.3\pm0.2$, then allowing the solution to equilibrate for at least 15 minutes;
    measuring the pH and adjusting the pH with acid if the pH is above 5.3;
    allowing the solution to equilibrate for at least 15 minutes; and
    repeating the steps of measuring the pH, adjusting the pH, and allowing the solution to equilibrate until the pH of the solution remains at pH $5.3\pm0.2$.

13. The method of claim 12, wherein the acid used to adjust the pH is selected from the group consisting of HCl, and $H_2SO_4$.

14. The method of claim 13, wherein said second solution is allowed to equilibrate for at least 30 minutes after each addition of acid.

15. The method of claim 14, wherein each solution is maintained at a temperature of from about 38° C. to about 42° C. until lyophilization is started.

16. A method of producing preliposomal Annamycin lyophilizate comprising the steps of:
adding DMPC, DMPG and polysorbate 20 to a mixture of pre-warmed water and t-butanol to prepare a first solution, wherein the prewarmed temperature is from about 35° C. to about 42° C., and wherein the ratio of water to t-butanol is from about 8:2 to about 9:1;
adjusting the pH of the first solution with one or more pharmaceutically acceptable acids to a pH of 4.8-5.9, such that the pH of the solution remains constant for about 15-90 minutes;
adding a second solution comprising approximately 8-12 wt. % of Annamycin in DMSO to the first solution, to provide a lipid containing solution of Annamycin;
sterile filtering the lipid containing solution of Annamycin; and
lyophilizing the lipid containing solution in individual aliquots to provide a preliposomal Annamycin lyophilizate wherein the Annamycin in the lyophilizate produced is at least 95% pure.

17. The method of claim 16, wherein the second solution comprises approximately 10 wt. % of Annamycin in DMSO, and the pH is 5.3±0.2.

* * * * *